(12) United States Patent
Leibitzki et al.

(10) Patent No.: US 9,084,860 B2
(45) Date of Patent: Jul. 21, 2015

(54) ARTIFICIAL NOSE COMPRISING A SPEECH VALVE

(75) Inventors: Harry Leibitzki, Blankenburg (DE); Steffen Suess, Halberstadt (DE)

(73) Assignee: PRIMED Halberstadt Medizintechnik GmbH, Halberstadt (DE)

( * ) Notice: Subject to any disclaimer, the term of this patent is extended or adjusted under 35 U.S.C. 154(b) by 0 days.

(21) Appl. No.: 13/878,643

(22) PCT Filed: Sep. 28, 2011

(86) PCT No.: PCT/DE2011/001807
§ 371 (c)(1),
(2), (4) Date: Apr. 12, 2013

(87) PCT Pub. No.: WO2012/048681
PCT Pub. Date: Apr. 19, 2012

(65) Prior Publication Data
US 2013/0192602 A1    Aug. 1, 2013

(30) Foreign Application Priority Data

Oct. 14, 2010 (DE) .......................... 10 2010 048 317

(51) Int. Cl.
| | |
|---|---|
| A62B 7/10 | (2006.01) |
| A61M 16/00 | (2006.01) |
| A61M 16/04 | (2006.01) |
| A61M 16/10 | (2006.01) |

(52) U.S. Cl.
CPC ......... *A61M 16/047* (2013.01); *A61M 16/0468* (2013.01); *A61M 16/1045* (2013.01)

(58) Field of Classification Search
CPC ....................................... A61F 2/20
USPC ............... 623/9; 128/200.26, 205.12–206.11, 128/207.14–207.29
See application file for complete search history.

(56) References Cited

U.S. PATENT DOCUMENTS

| | | | |
|---|---|---|---|
| 2,996,071 A | 8/1961 | Takaoka | |
| 4,582,058 A * | 4/1986 | Depel et al. ............. | 128/207.17 |
| 5,738,095 A | 4/1998 | Persson | |
| 6,422,235 B1 | 7/2002 | Persson | |
| 6,772,758 B2 | 8/2004 | Lambert | |

FOREIGN PATENT DOCUMENTS

| | | |
|---|---|---|
| DE | 694 05 587 | 2/1998 |
| DE | 699 20 440 | 10/2005 |
| WO | WO-99/29268 | 6/1999 |
| WO | WO-2008/132222 | 11/2008 |
| WO | WO-2010/060983 | 6/2010 |
| WO | WO-2011/144237 | 11/2011 |

* cited by examiner

*Primary Examiner* — Yashita Sharma
(74) *Attorney, Agent, or Firm* — Jordan and Hamburg LLP

(57) ABSTRACT

A device for inserting into a tracheostoma prosthesis or a thracheostoma plaster comprises a cylindrical housing and a cylindrical valve element, the housing is provided with a first opening for the connection to the stoma of the patient and with at least one second opening on the opposite side, and the valve element in the second opening of the housing is provided to close the second opening. The valve element is configured so that it can be closed manually by means of a finger and can be opened by elastic return, and the housing surrounds the valve element and the valve element receives a moisture and heat exchanging filter. A cylindrical spring element is arranged between the housing and the valve element.

8 Claims, 3 Drawing Sheets

ARTIFICIAL NOSE COMPRISING A SPEECH VALVE

BACKGROUND OF THE INVENTION

This invention relates to an artificial nose comprising a speech valve in the form of a device for inserting into a tracheostoma prosthesis or tracheostoma plaster.

Tracheostoma prostheses (also known as tracheal cannulas or tracheostoma tubes) for treating patients without larynx (laryngeetomees) with opened throat (so called tracheostoma) have been known for decades. These prostheses are available with and without a speech valve. However, the different embodiments provided with a speech valve have become more and more important in the rehabilitation of laryngectomees because they make speaking success possible for the patients.

The tracheostoma tubes with a speech valve mostly consist of a treacheal cannula with a cannula plate and a valve receiving part for supporting an exterior speech valve, and an interior speech valve of the tracheal cannula is supported in a tube between the esophagus and the windpipe so that air can escape through the interior speech valve towards the mouth area if the tracheostoma is blocked (in case of a closed exterior speech valve) and vibrations for speaking are generated in the upper area of the esophagus. In these arrangements, the tracheostoma is blocked manually by closing the exterior speech valve at the outer face of the tracheal cannula.

Due to a laryngectomy and the subsequent implant of a tracheostoma prosthesis, the connection between the nose and the lung of the laryngectomee is interrupted so that the natural function of the nose (warming, moisturizing and filtering the respiratory air as well as setting up a known respiratory resistance) is not guaranteed any more.

According to the current state of the art, heat and moisture exchangers (also called artificial nose or HME) are known to be put on tracheal cannulas or tracheostoma tubes.

The heat and moisture exchangers extract moisture and heat from the patient's exhaled air and deliver them to the inhaled air simultaneously filtering the respiratory air so that the penetration of particles into the patient's respiratory tract is prevented and a known respiratory resistance is set up.

DE 694 05 587 T2 discloses an arrangement for inserting a tracheostoma with a filter housing for receiving a filter that exchanges moisture and heat, and the filter housing is configured with a first opening for the connection to the patient's stoma and with at least a second opening arranged at the opposite side of the filter in one flow direction of the respiratory air. In this arrangement, a valve element is provided in the second opening of the filter housing and is suitable for closing said opening manually by means of a finger and for opening it by elastic return.

SUMMARY OF THE INVENTION

The aim of the present invention is to provide a device for inserting into a tracheostoma, enabling the laryngectomee to speak with the aid of inhaled and exhaled respiratory air, for simultaneously warming up, moisturizing and filtering the respiratory air and setting up a known respiratory resistance, and also preventing at the same time salvia from flowing into the trachea so that the patient's respiratory tract is protected and the patient's need to cough as a consequence of speaking is inhibited. In particular, bigger particles shall be removed via the installed filter by a kind of self-cleaning when the device is used as intended.

Said aim is achieved by a device to be inserted into a tracheostoma according to the first claim. Advantageous embodiments of this invention are specified in the sub-claims.

The nature of this invention is to provide a novel device to be inserted into a tracheostoma prosthesis or a tracheostoma plaster and said device comprises a housing and a valve element, the housing is provided with a first opening for the connection to the stoma of a patient and with at least one second opening at the opposite side, the valve element is positioned in the second opening of the housing to close the second opening and is configured so that it can be closed manually by means of a finger and can be opened by elastic return, and the housing surrounds the valve element that receives a heat and moisture exchanging filter, and a cylindrical spring element is arranged between the housing and the valve element, According to this invention, the housing is equipped with an upper and a lower guide ring and guide rods with lateral recesses (openings) are arranged between said guide rings enabling the passage of respiratory air.

The inventive valve element is provided with a cover and a wall with lateral recesses and the position and shape of said recesses correspond to the openings of the housing so that respiratory air can pass through them if the device is used as intended. At least two guide projections are provided at the wall under the cover and engage into the recesses of the guide rods of the housing so that the guide projections are movable in the guide rods between two terminal points.

The filter is arranged between the cover and the wall of the valve element and the spring element is supported under the filter between the valve element and the housing.

The inventive device is made of plastic material as a disposable item and can be easily coupled with known tracheal cannulas, tracheostoma tubes or trachestoma plasters because the outside wall of the housing has a common diameter and is provided with a bulge at the side facing the stoma so that the device can be mounted and fixed on the tracheal cannulas, tracheostoma tubes or tracheostoma plasters.

The advantage of the inventive device is that the filter protrudes out of the housing up to the outer edge of the housing so that rough particles in the inhaled air are retained in the recesses and led out during exhalation thus preventing the rapid clogging of the device.

Moreover, the inventive device has the advantage that it has a very flat design and, if used as intended, it shows better breath parameters than the devices of the state of the art due to its recesses for the air outlet.

The invention will be explained in more detail with reference to the following embodiment and figures.

DETAILED DESCRIPTION OF THE INVENTION

Figure 1A:
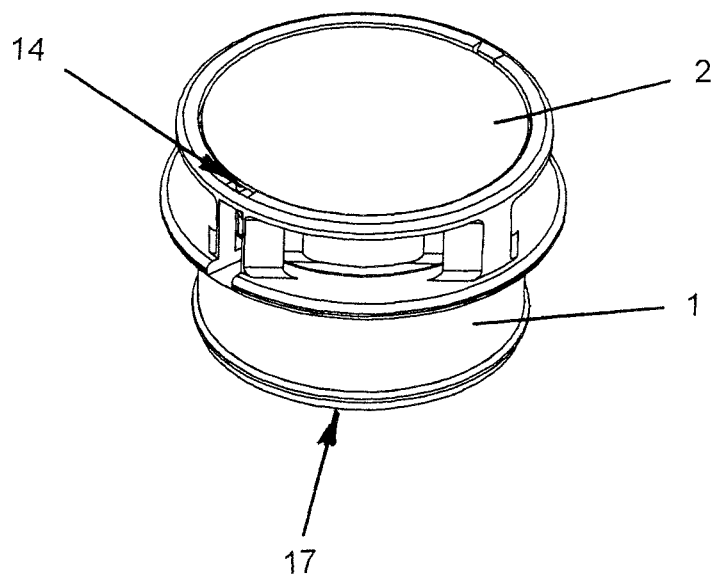
FIG. 1a is a schematic 3D view of an embodiment of an inventive device in a first viewing direction.
Figure 1B:
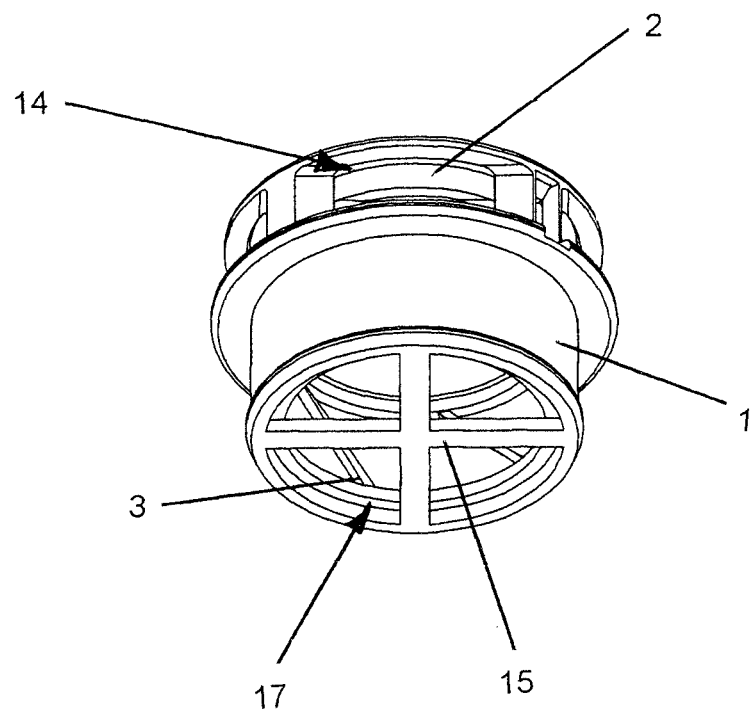
FIG. 1b is a schematic 3D view of the embodiment of the inventive device according to FIG. 1 in a second viewing direction.

FIGS. 1a and 1b show a device for inserting a tracheostoma prosthesis or a thracheostoma plaster comprising a cylindrical housing (1) and a cylindrical valve element (2), the housing (1) is provided with a first opening (17) for the connection to the patient's stoma and with at least one second opening (14) on the opposite side, and the valve element (2) in the second opening (14) of the housing (1) is provided to close the second opening (14) and is configured so to be closed manually by means of a finger and to be opened by elastic return, In this arrangement, the housing (1) surrounds the valve element (2).

The valve element (2) receives a heat and moisture exchanging filter (not shown in the figure), and a cylindrical spring element (3) is positioned under the filter between the housing (1) and the valve element (2).

Figure 2A:
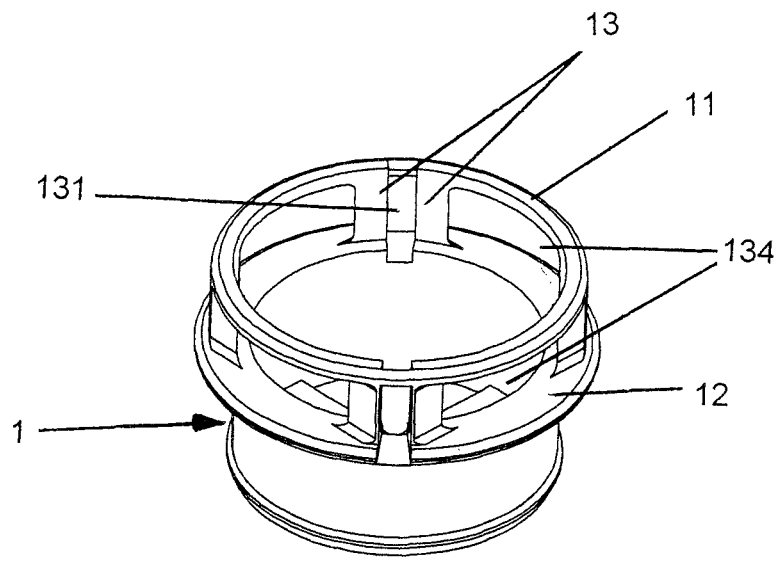
FIG. 2a is a schematic 3D view of the housing according to FIGS. 1a and 1b.

As shown in FIG. 2a, the housing (1) is equipped with an upper guide ring (11) and a lower guide ring (12) and guide rods (13) are arranged in pairs between said rings and have recesses in between (131) and lateral openings (134) are provided between the pairwise guide rods (13) so that air can be led in and out through them.

Figure 2B:
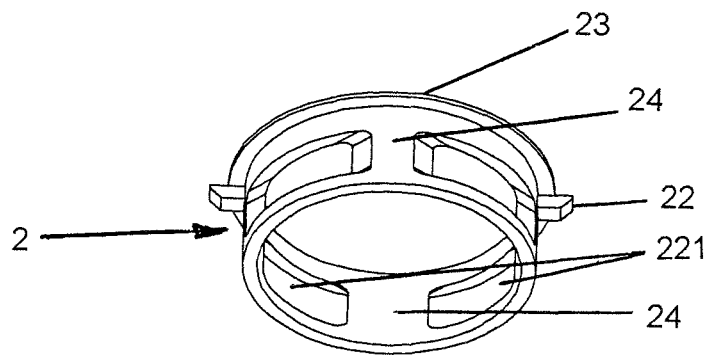
FIG. 2b is a schematic 3D view of the valve element according to FIGS. 1a and 1b.
Figure 2C:
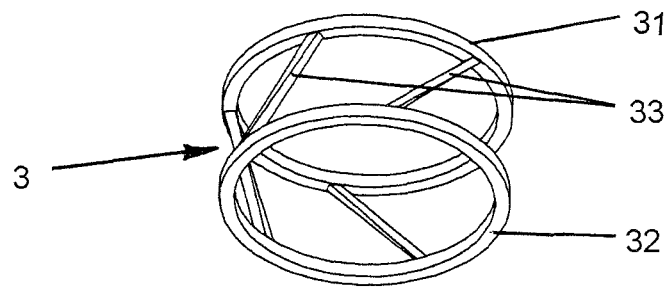
FIG. 2c is a schematic 3D view of the spring element according to FIGS. 1a and 1b.

As shown in FIG. 2b, the valve element (2) is provided with a cover (23) and a wall (24) with lateral recesses (221) and the position and shape of said recesses (221) correspond to the lateral openings (134) of the housing (1), and at least two guide projections (22) are arranged at the wall (24) under the cover (23) and engage into the recesses (131) of the guide rods (13) of the housing (1). The guide projections (22) are movable in the guide rods (13) between two terminal points.

The filter not shown in the drawing is surrounded by the valve element (2). It is positioned between the cover (23) and the wall (24) of the valve element (2) and the spring element (3) shown in FIG. 3c is arranged under the filter between the housing (1) and the valve element (2).

The housing (1) is provided with radial arms (15) on the opposite side of the guide rings (11; 12).

Figure 3A:
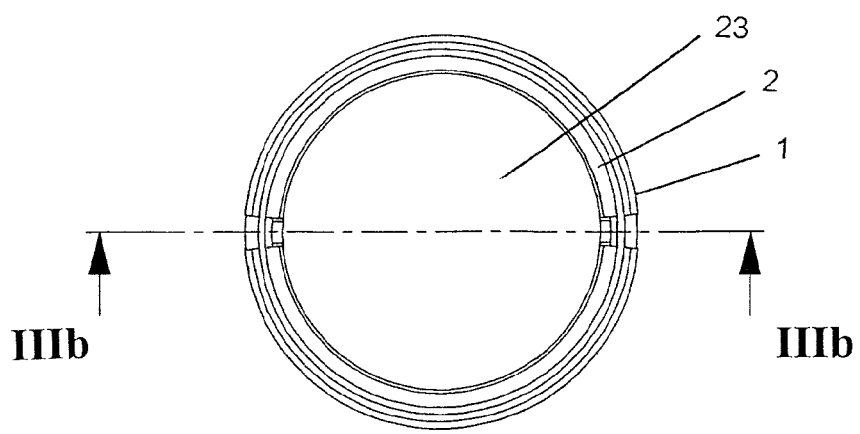
FIG. 3a is a top view of the device according to FIG. 1.

The spring element (3) shown in FIG. 3c consists of an upper spring ring (31) and a lower spring ring (32) and the spring rings (31 and 32) are connected with each other via elastic spring arms (33).

The lower edge of the wall (24) of the valve element (2) and the radial arms (15) of the housing (1) support the spring rings (31 and 32).

The guide projections (22) are movable between the recesses (131) of the guide rods (13) between two terminal points.

The inventive device is advantageously a disposable product made of plastic material.

Thus, the housing (1) and the valve element (2) are made, for example, of polyethylene (PE) or polypropylene (PP).

The spring element (3) is made, for example, of polypropylene (PP) or polyethylene (PE). As an alternative, it can also be designed as a spiral spring made of medically suited metal such as spring steel.

The filter is made, for example, of foamed polyurethane.

If the inventive device is used as intended, the filter is arranged in the valve element (2) in such a manner that the spring element (3) is positioned under the filter, the upper spring ring (31) of the spring element (3) is supported at the lower end of the wall (24) of the valve element (2) and the lower spring ring (32) of the spring element (3) is supported at the arms (15) of the housing (1).

The spring element can be compressed (pressed position of the spring element) or released (not pressed position of the spring element) via the movable spring arms (33) resulting in the closing or opening of the second opening (14) in the housing (1) by means of the cover (23) of the valve element (2).

Figure 3B:
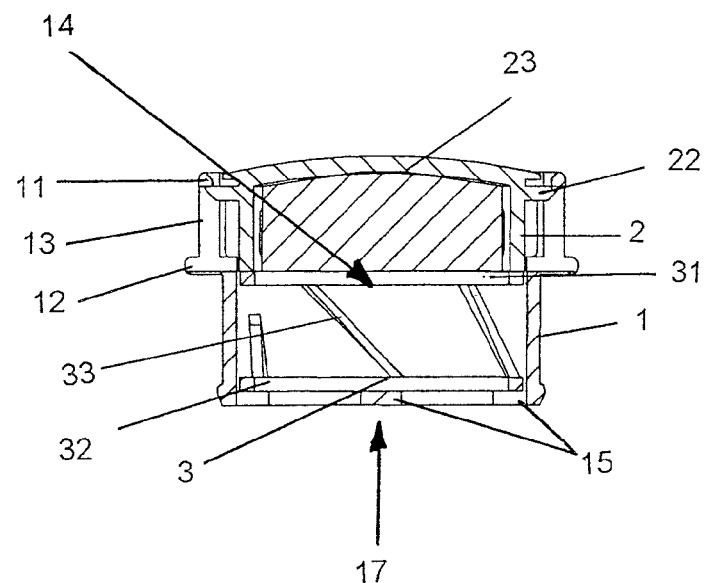
FIG. 3b is a sectional view of the device along the plane IIIb-IIIb in FIG. 3a with pressed spring element (corresponds to the closed state of the device).

For speaking, the cover (23) is slightly pressed by the aid of the patient's finger so that the aforementioned closing action between the second opening (14) and the cover (23) is generated (see FIG. 3b). After speaking, the finger is taken away so that the cover (23), which has been moved due to the force of the spring, releases the second opening (14) again and the respiratory air can pass through the lateral recesses (221) of the valve element (2) and the lateral openings (14) of the housing (1). During inhaling, the filter positioned in the valve element (2) retains particles [particularly in the area of the openings (14)] that are blown out by the filter during exhaling so that the clogging of the the filter is prevented.

All features disclosed in the description, the embodiments and the subsequent claims can be important for the invention both individually and in any combination.

The invention claimed is:

1. A device for inserting a tracheostoma prosthesis or a tracheostoma plaster comprising
   a cylindrical housing and a cylindrical valve element;
   the housing being provided on a first side thereof with a first opening for connection to a patient's stoma and with at least one second opening on a second side thereof, opposite the first side;
   a valve element in the second opening of the housing, the valve element being provided to close the second opening;
   the valve element being configured so as to be closable manually by means of a finger and openable by elastic return;
   the housing surrounding the valve element, the valve element being adapted to receive a heat and moisture exchanging filter; and
   a cylindrical spring element arranged between the housing and the valve element, in which
      the housing is equipped with an upper guide ring and a lower guide ring;
      guide rods are arranged in pairs between said rings and have recesses in between said rings;
      lateral openings are provided between the pair of guide rods;
      the valve element is provided with a cover and a wall with lateral recesses, the position and shape of said recesses corresponding to the lateral openings of the housing; and
   at the wall, under the cover, at least two guide projections are arranged that engage into the recesses of the guide rods of the housing, the valve element being movable to close or open the second opening whereupon closing of the second opening enables a user of the device to use the device to speak through the device and opening of the second opening enables correspondence of the position and shape of the lateral recesses of the valve element with the lateral openings of the housing so that a user of the device may use the device to breathe through the device.

2. The device according to claim 1, wherein
   the filter, which is adapted for receipt by the valve element, is positioned between the cover and the wall of the valve element and
   the spring element is arranged under the filter between the housing and the valve element.

3. The device according to claim 1, wherein the housing is provided with radial arms on the opposite side of the guide rings.

4. The device according to claim 1, wherein the spring element is constituted of an upper spring ring and a lower spring ring and the spring rings are connected with each other by elastic spring arms.

5. The device according to claim 4, wherein
- a lower edge of the wall of the valve element and of the housing support the spring rings; and
- the guide projections engaging in the recesses of the guide rods are movable between two terminal points.

6. The device according to claim 1, wherein the housing and the valve element are made of polyethylene or polypropylene.

7. The device according to claim 1, wherein the spring element is made of polyethylene or polypropylene or spring steel.

8. The device according to claim 1, wherein the filter is made of foamed polyurethane.

* * * * *